(12) United States Patent
Yin

(10) Patent No.: US 9,289,129 B2
(45) Date of Patent: Mar. 22, 2016

(54) NON-CONTACT MEASURING METHOD AND APPARATUS IN PEDIATRICS

(71) Applicant: IMAGE TECHNOLOGY INC., Ji'nan (CN)

(72) Inventor: Shi Yin, Markham (CA)

(73) Assignee: IMAGE TECHNOLOGY INC., Ji'Nan (CN)

(*) Notice: Subject to any disclaimer, the term of this patent is extended or adjusted under 35 U.S.C. 154(b) by 176 days.

(21) Appl. No.: 14/059,112

(22) Filed: Oct. 21, 2013

(65) Prior Publication Data

US 2014/0114192 A1    Apr. 24, 2014

Related U.S. Application Data

(63) Continuation of application No. PCT/CN2012/083258, filed on Oct. 20, 2012.

(51) Int. Cl.
 *A61B 5/05* (2006.01)
 *A61B 5/00* (2006.01)
 *A61B 5/107* (2006.01)

(52) U.S. Cl.
 CPC ............ *A61B 5/0077* (2013.01); *A61B 5/0064* (2013.01); *A61B 5/1075* (2013.01); *A61B 5/448* (2013.01); *A61B 2503/04* (2013.01); *A61B 2503/06* (2013.01)

(58) Field of Classification Search
 CPC ........ A61B 5/055; A61B 6/547; A61B 19/52; A61B 17/16; A61B 19/50
 See application file for complete search history.

(56) References Cited

U.S. PATENT DOCUMENTS

| | | | |
|---|---|---|---|
| 6,358,208 B1 * | 3/2002 | Lang et al. | 600/438 |
| 2005/0203384 A1 * | 9/2005 | Sati et al. | 600/426 |
| 2014/0193336 A1 * | 7/2014 | Rousso et al. | 424/1.65 |

* cited by examiner

*Primary Examiner* — Joel Lamprecht
(74) *Attorney, Agent, or Firm* — Hauptman Ham, LLP

(57) ABSTRACT

A non-contact measuring method in pediatrics is disclosed. An infant model is established by acquiring a human image and a depth image of a subject infant; updating the infant model by acquiring a plurality of anthropometric characteristic points and finally obtaining an anthropometric data of the subject infant from the updated infant model. This invention also provides an apparatus to achieve the above mentioned measuring method. An infant model which includes anthropometric characteristic points and 3D surface models is established based on a human image acquired by an image acquisition module and a depth image acquired by a depth information acquisition module in conjunction with an algorithm program built in a data acquisition and processing module. Human anthropometric data is obtained by analyzing the infant model. The non-contact measuring method and measuring apparatus in pediatrics make the measuring process more humane without contacting a subject body.

14 Claims, 5 Drawing Sheets

NON-CONTACT MEASURING METHOD AND APPARATUS IN PEDIATRICS

CROSS REFERENCE TO RELATED APPLICATION

This bypass application claims the priority of International Application No. PCT/CN2012/083258 filed on Oct. 20, 2012.

FIELD OF THE INVENTION

The present invention relates to a measuring method in pediatrics, in particular, a non-contact measuring method in pediatrics. The present invention also relates to a non-contact measuring apparatus in pediatrics.

BACKGROUND OF THE INVENTION

Height/length, weight, head circumference, chest circumference, sitting height and some other anthropometric data are the important growth indicators set forth in child growth standards published by the World Health Organization for evaluating the children's development and growth conditions, and need to be monitored regularly. Because children's growth status and physical indicators such as height, weight and the like are closely related to children' health, the above anthropometric data are the key indicators, and need to be monitored in the process of growing infants and young children.

From the early 20th century, contact measuring methods have been used for measurement in pediatrics, and never changed. Measuring apparatus improvements in pediatrics have also focused on contact measuring apparatuses. For example, portable weighing scales for measuring infants' weight, portable soft rulers for measuring infants' and children's height/length, and so on are the early measuring apparatus in pediatrics. With the development of medical apparatus, measuring apparatus in pediatrics gradually developed from a manual reading into automatically intelligent measurement; a plurality of independent measuring apparatus has gradually integrated and developed into intelligent apparatus which is able to measure weight, length, head circumference, and other indicators simultaneously. The intelligent medical measuring apparatus disclosed in Chinese Utility Model Patent No. ZL 200920084234.3 includes a weighing unit, a measuring unit for height/length and sitting height, a head circumference-measuring unit, a chest circumference-measuring unit, etc, wherein the weight sensor of the weighing unit is fixed to the base of the medical measuring apparatus, the other end of the weight sensor supports a measuring bed as a weighing table, and the weight sensor is coupled with a microprocessor through an A/D conversion circuit. The left end of the measuring bed is provided with a curved board for a head while the right end of the bed is provided with a curved board for feet. A curved board for feet is provided with an infrared receiver and a data reset contact. The both lateral sides of the bed are provided with railings with scales. The inner of the railings are provided with sliding rails, and the upper of the sliding rails are provided with a mobile data acquisition box used for acquiring data of lengths and sitting heights. The head circumference ruler in the head circumference measuring unit and the chest circumference ruler in the chest circumference measuring unit are individually disposed in the positions on the bed near the curved board for a head and slightly distant from the curved board for a head. The mobile data acquisition box for acquiring data of length and sitting height, head circumference ruler and chest circumference ruler are respectively coupled with the microprocessor through an interface circuit. The intelligent medical measuring apparatus can simultaneously measure various anthropometric data, such as an infant's head circumference, chest circumference, weight, height, sitting height, etc, but this type of apparatus is still a contact measuring apparatus, so that there are some mandatory requirements for the infant's body pose in the measuring process. For instance, infants or young children have to straighten the limbs in the measuring process, or a ruler has to physically contact infants or young children. However, since infants can not cooperate effectively. There is a great difficulty in the measuring process, and the accuracy of measurement results is affected.

Although a few simple non-contact measuring apparatuses have appeared in recent years, such apparatuses are mainly designed for adults, and do not apply to infants and young children suitably, especially to infants unable to stand. Therefore, infants can not collaborate effectively, making the measuring process laborious, and increasing the difficulty of measuring.

SUMMARY OF THE INVENTION

The most important technical objective of the present invention is to provide a non-contact measuring method in pediatrics used for obtaining anthropometric data from infant body models.

Furthermore, the technical objective of the present invention is to provide a non-contact measuring apparatus in pediatrics using the foregoing method to conduct measurement.

To achieve the above objectives, the first technical solution of the present invention provides a non-contact measuring method in pediatrics. The method comprises the steps of: acquiring a human image and a depth image of a subject infant; establishing an infant body model based on the acquired human image and the depth image; acquiring data of a plurality of anthropometric characteristic points of the subject infant, and updating the infant body model based on the acquired data of the anthropometric characteristic points, and obtaining anthropometric data of the subject infant from the updated infant body model.

The second technical solution of the present invention provides another non-contact measuring method in pediatrics comprising the steps of: (1) inputting an identity information of a subject infant; (2) generating a basic infant body model based on the identity information and a weight information of the subject infant; (3) acquiring data of a depth image and a human image of the subject infant; (4) calculating anthropometric characteristic points of the subject infant based on the acquired data of the images and the basic infant body model, and updating the infant body model based on the calculated anthropometric characteristic points; (5) examining the infant body model completion, returning to Step (3) to continuously acquire data of another frame of the depth image and another frame of the human image from video signals if the infant body model is not completed, and going to Step (6) if the infant body model is complete; and (6) obtaining the anthropometric characteristic data of the subject infant from the updated infant body model.

Preferably, in Step (1), the inputted identity information of the subject infant comprises names, gender, dates of birth and gestational age.

Preferably, in Step (2), the infant body model is obtained directly from an infant body model database, and the infant body model database comprises the basic infant body model which is composed of the anthropometric characteristic points and the 3D surface models.

Preferably, in Step (3), each of the depth image and the human image is one frame of video signals.

Preferably, in Step (4), the anthropometric characteristic points of the subject infant are calculated based on the acquired image data and the infant body model.

The foregoing Step (4) further comprises sub-steps of: (41) executing a background modeling via the depth image and the human image; (42) executing a synchronization process to the human image and the depth image, wherein the process comprises a matching process between the human image and the depth image; (43) executing a foreground separation based on the results of Step (41) and Step (42); (44) executing torso detection to a result obtained in Step 43 in conjunction with the subject infant body model, and calculating to determine each anthropometric characteristic point.

Preferably, in Step (5), the completion of the updated infant body model is examined based on anthropometry.

Preferably, in Step (5), the stability of each anthropometric characteristic point is examined by using multi-frame human images and depth images based on video processing technology.

Preferably, in Step (6), the anthropometric data of the subject infant are calculated and obtained by using the anthropometric characteristic points in conjunction with the 3D surface models.

Preferably, Step (7) is further included after Step (6). In Step (7), according to a result of Step (6), data in the infant body model database are updated by using an intermediate result and a final result of anthropometry.

Moreover, the present invention also provides a non-contact measuring apparatus in pediatrics for archiving the foregoing measuring method. The measuring apparatus comprises a data acquisition and processing unit, one or more of depth information acquisition modules coupled to the data acquisition and processing unit for acquiring the depth image of the subject infant, one or more image acquisition modules coupled to the data acquisition and processing unit, and a data output module bidirectionally coupled to the data acquisition and processing unit.

Preferably, the data acquisition and processing unit is provided with a built-in algorithm program used for establishing the infant body model, and an algorithm program used for obtaining anthropometric data from the infant body model. The infant body model comprises multiple anthropometric characteristic points and 3D surface models.

Preferably, the non-contact measuring apparatus in pediatrics further comprises one or more ultrasonic sensors for sensing a hair thickness and a cloth thickness, and the ultrasonic sensors and the data acquisition and processing unit are bidirectionally coupled with each other.

Preferably, the non-contact measuring apparatus in pediatrics further comprises a bed for the subject infant.

Preferably, the multiple depth acquisition modules and the image acquisition modules are respectively disposed above the bed, on the head side and/or lateral side of the bed, ultrasonic sensors are respectively disposed at the end of the head side, on the lateral side or at the end of a foot side of the bed.

Preferably, the non-contact measuring apparatus in pediatrics further comprises a weighing sensor disposed under the bottom of the bed, and the weighing sensor is coupled with the data acquisition and processing unit.

The present invention provides a non-contact measuring method and apparatus in pediatrics which establish an infant body model comprising multiple anthropometric characteristic points and 3D surface models by obtaining the depth data of the subject infant and human image/video data, and eventually obtain anthropometric characteristic data of the subject infant, such as height/length, head circumference, chest circumference and so on, by analyzing the infant body model established, wherein after the anthropometric infant body model is obtained, the infant body model can also be corrected to obtain more accurate measurement data by removing the infant's hair thickness and cloth thickness. In the measuring process, the non-contact measuring method and measuring apparatus in pediatrics make the measuring process more humane without contacting a subject body.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENTS

The content of the present invention is described in detail by reference to embodiments below in conjunction with the accompanying drawings.

In a non-contact measuring method in pediatrics provided by the present invention, an infant body model is established by obtaining a human image and a depth image of a subject infant, and modeling a human body by a dedicated measuring apparatus. Anthropometric characteristic data of the subject infant, such as height, head circumference, chest circumference and so on, are obtained from the infant body model eventually. In the non-contact measuring method in pediatrics, the measuring apparatus is not required to contact the body of the infant, and the infant does not have to keep the same specific pose, thereby making the measuring process more humane.

Figure 1:
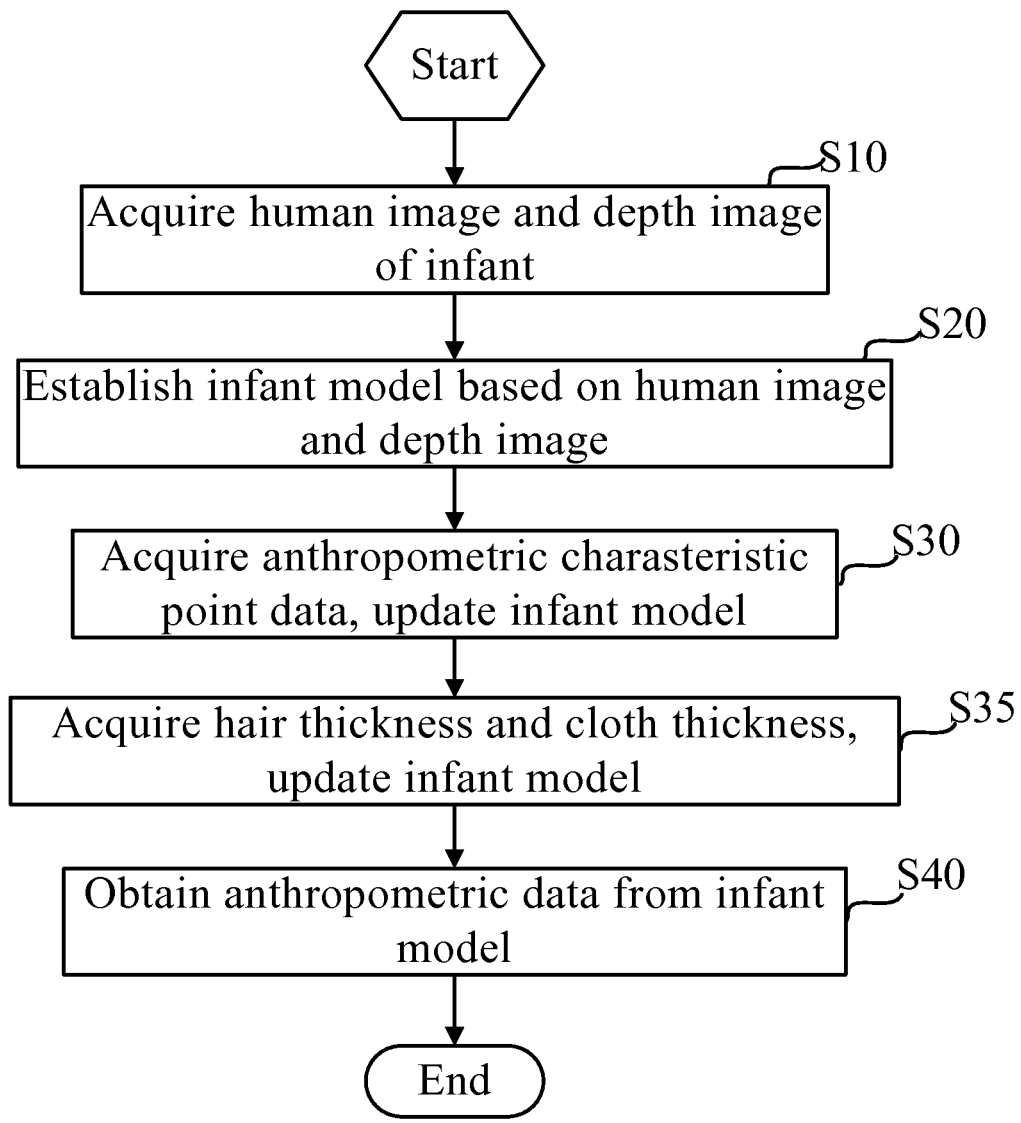
FIG. 1 is a schematic block diagram illustrating a measurement principle of a non-contact measuring method in pediatrics of the present invention.

As shown in FIG. 1, the first embodiment of the non-contact measuring method in pediatrics comprises the following steps : Step S10: A human image and a depth image of a subject infant are acquired; Step S20: An infant body model is established based on the acquired human image and the depth image; Step S30: Data of a plurality of anthropometric characteristic points of the subject infant are calculated, and the infant body model is updated based on the calculated data of the anthropometric characteristic points; Step S35: Data of the subject infant's hair thickness and cloth thickness are acquired and the infant body model is updated based on the acquired data of the hair thickness and cloth thickness; and Step S40: Anthropometric data of the subject infant is obtained from the updated infant body model.

In the non-contact measuring method in pediatrics described above, the subject infant's human image and depth image are acquired and an initial infant body model is established in step S10 and step S20. The infant body model indicates a model composed of a plurality of anthropometric characteristic points and 3D surface models. The data of multiple anthropometric characteristic points of the subject infant are obtained, and the infant body model is updated, so that the accurate infant body model is obtained in the step S30. In the process of step S30 of acquiring the data of the anthropometric characteristic points and updating the infant body model, the following sub-steps are included: S31: Data of anthropometric characteristic points of the subject infant are obtained, and the infant body model is updated based on the data of the anthropometric characteristic points; S32: Whether the multiple anthropometric characteristic points in the infant body model are all used for modeling is determined If yes, the process continues to Step 35, and if not, the process returns to Step 31 for acquiring data of next anthropometric characteristic points; Step 35: The data of the subject infant's hair thickness and cloth thickness are acquired, and the infant body model is updated based on the acquired data of the hair thickness and cloth thickness. The more accurate infant body model is obtained through updates of Step 30 and Step 35. Finally, the infant's anthropometric data, such as, length/height, head circumference, chest and so on, are obtained by analyzing the established infant body model.

During the process of the implementation process of this measuring method, in Step 10 and Step 20, the infant's human images and depth images can be obtained via image acquisition modules and distance measuring modules, respectively. A plurality of human images can also be obtained via image acquisition modules in combination with standard backgrounds. Three-dimensional data can be obtained by analyzing the human images. For example, by placing an infant in an medical bed for infants with rulers or reference points, the 3D data of the infant can be analyzed and obtained via the reference points combined with the image background, or via the distances between each body part of the infant and the depth information acquisition modules, which are measured by the depth information acquisition modules. In Step 30 and Step 35, the number of the acquisition modules for acquiring the data of anthropometric characteristic points and the number of the acquisition modules for acquiring the data of the infant's hair thickness and cloth thickness can be determined based on measurement accuracy, ease of operation and so on. In actual measurements, the infant's hair thickness and cloth thickness can be obtained via ultrasonic sensors, and the anthropometric characteristic points of the infant body model can be obtained via the acquisition modules disposed near the positions of the anthropometric characteristic points.

Figure 2:
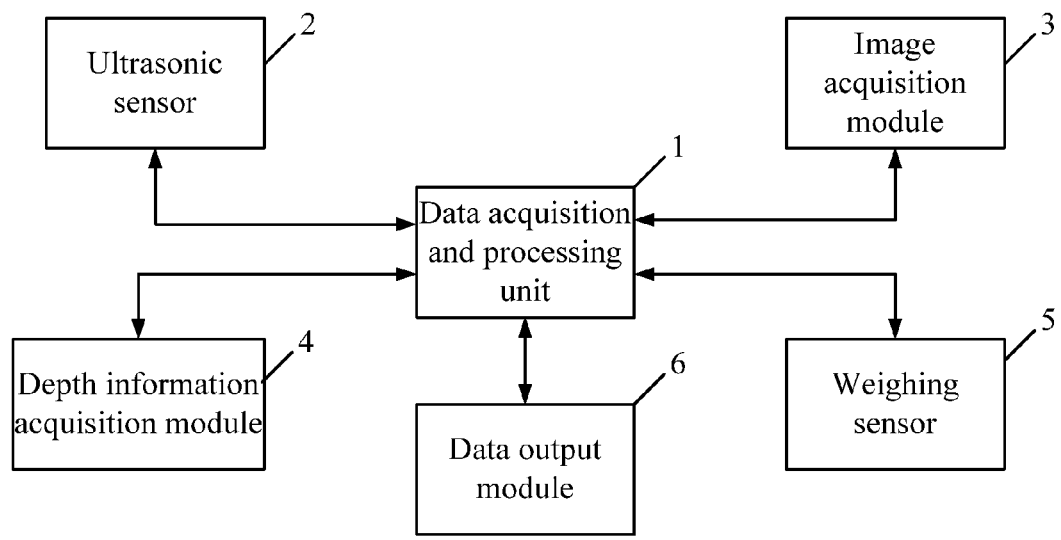
FIG. 2 is a schematic block diagram of a structure of a non-contact measuring apparatus in pediatrics of accordance with the present invention.

The first embodiment of the non-contact measuring method in pediatrics is described above while the non-contact measuring apparatus in pediatrics provided by the present invention will be described below in combination with the diagram. As shown in FIG. 2, the non-contact measuring apparatus in pediatrics comprises an data acquisition and processing unit 1, one or more ultrasonic sensors 2 bidirectionally coupleed to the data acquisition and processing unit 1, one or more image acquisition modules 3, one or more depth information acquisition modules 4, and a data output module 6. The data acquisition and processing unit is an integrated processor provided with an algorithm program for establishing the anthropometric characteristic points and the infant body models of the subject infant, and an algorithm program for obtaining the anthropometric data from the infant body models. The data acquisition and processing unit 1 includes a data storage module for storing an established infant body model database and the anthropometric data. Specifically, the infant body model comprises a plurality of anthropometric characteristic points and 3D surface models. The image acquisition modules 3 are used for acquiring the human images of the subject infant, color images are preferred. The depth information acquisition modules 4 are used for acquiring the depth images of the subject infant. The acquisition and processing unit 1 establishes the infant body models by analyzing the data of the human images and the depth images. By analyzing the ultrasounds transmitted and received by the ultrasonic sensors 2, the non-contact measuring apparatus in pediatrics can measure the positions of the infant's head and body, obtain the hair thickness and cloth thickness, and correct the established infant body model. The data acquisition and processing unit eventually analyzes and obtains the anthropometric data from the corrected human model via the built-in algorithm program for anthropometry. The data output module includes a monitor, a printer and so on for displaying the measurement results to doctors or family members, or printing the measurement results.

Figure 3:
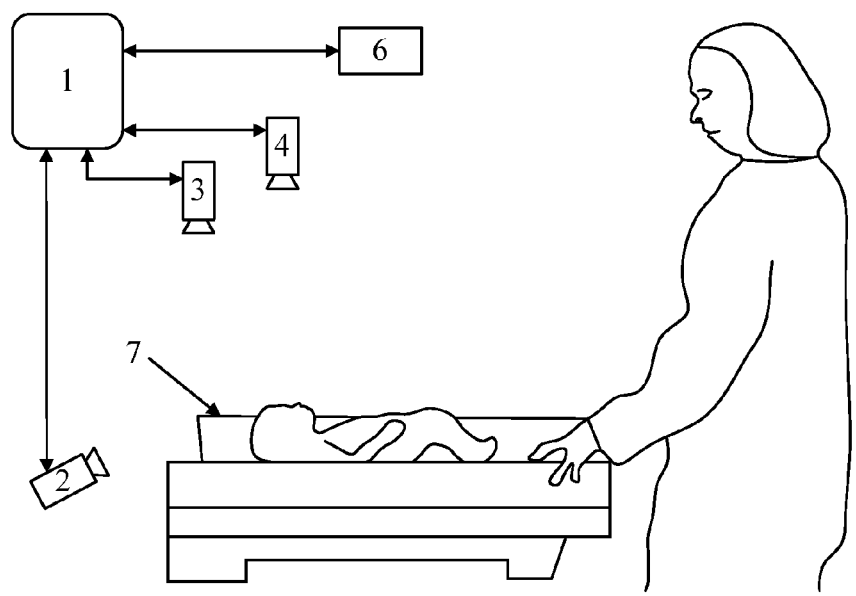
FIG. 3 is a schematic diagram of a use state of a non-contact measuring apparatus in pediatrics shown in FIG. 2.

As show in FIG. 3, the non-contact measurement apparatus in pediatrics further comprises a bed 7 for the subject infant to be put in. A weighing sensor 5 is also disposed under the bottom of the bed 7. The weighing sensor 5 is coupled with the acquisition and processing unit 1. The multiple image acquisition modules 3 are respectively disposed at the end of the bed 7 where the infant's head is placed, on the lateral sides of the bed 7 and above the bed 7. The multiple depth information acquisition modules 4 are respectively disposed in the positions surrounding the bed 7. Similarly, for measuring the hair and cloth thickness, the ultrasonic sensors 2 are required to be disposed in the positions near the infant's head, above the infant's body and in the positions near the infant's feet. Specifically, one or more ultrasonic sensors 2 are disposed at the end of the bed 7 where the infant's head is placed, on the lateral side of the bed, or at the end of the bed for being placed with the infant's feet. The specific numbers of the image acquisition modules 3, the depth information modules 4 and the ultrasonic sensors 2 can be changed based on measurement accuracy, ease of operation, and so on.

Figure 4:
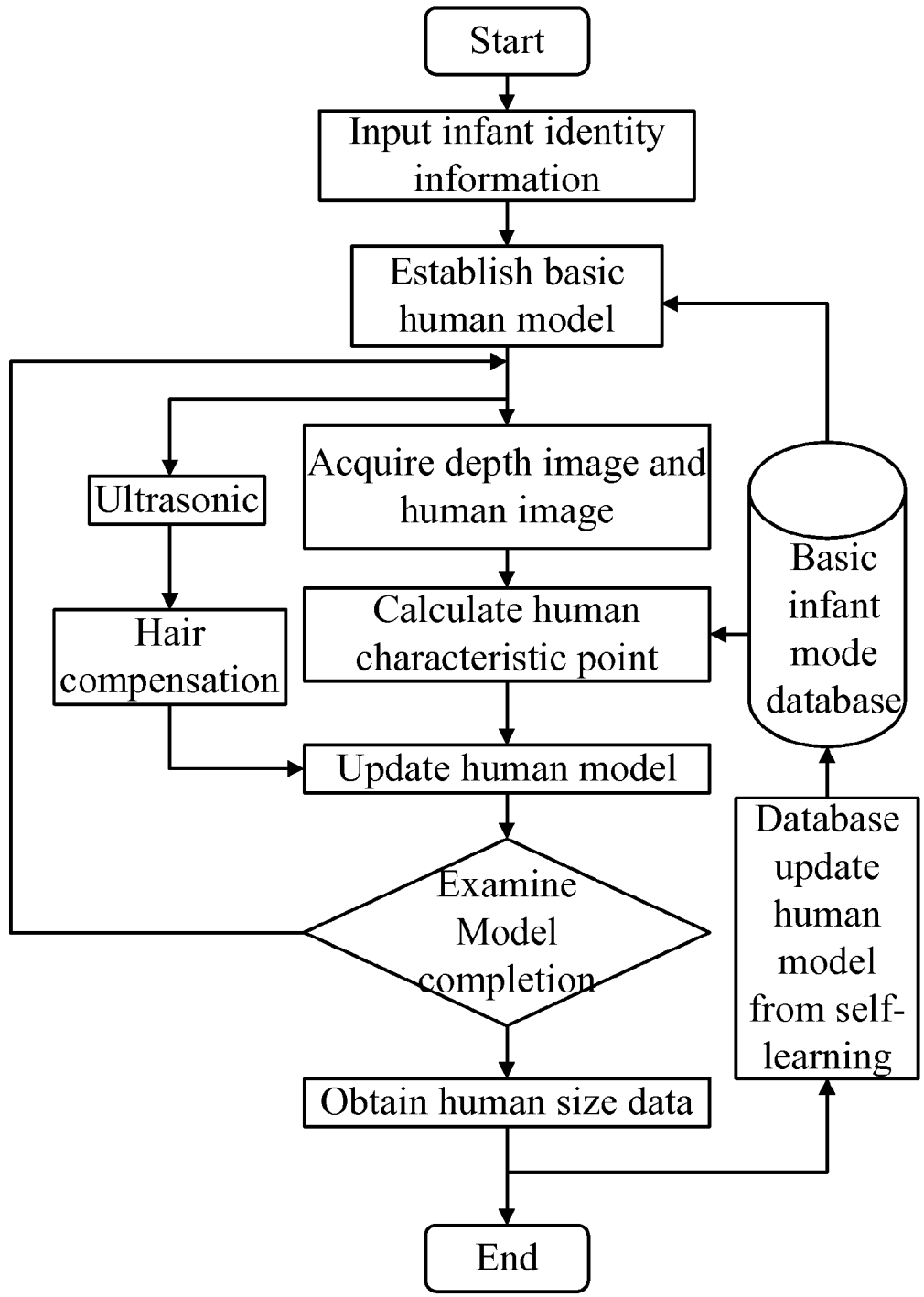
FIG. 4 is a schematic diagram illustrating a second embodiment of a non-contact measuring method in pediatrics.

According to the non-contact measuring apparatus in pediatrics, a non-contact measuring method provided by the present invention further includes a second embodiment. As shown in FIG. 4, the second embodiment specifically comprises the following steps of: (1) inputting an identity information of a subject infant; (2) generating a basic infant body model based on the identity information and a weight information of the subject infant; (3) acquiring data of a depth image and a human image of the subject infant; (4) calculating the anthropometric characteristic points of the subject infant based on the acquired data of the image and the basic infant body model, and updating the infant body model based on the calculated anthropometric characteristic points; (5) examining the infant body model completion, returning to the Step (3) to continuously acquire data of another frame of the depth image and another frame of the human image from video signals if the infant body model is not completed, and going to Step (6) if the infant body model is complete; and (6) obtaining the anthropometric characteristic data of the subject infant from the updated infant body model.

In Step (1), the inputted identity information of the subject infant comprises names, gender, dates of birth and gestational age. The measurement file are created with the identity information, wherein all or a part of the identity information may also be used to generate the basic infant body model.

In Step (2), the infant body model is obtained directly from an infant body model database, and the infant body model database comprises the basic infant body model which is composed of the anthropometric characteristic points and the 3D surface models.

In Step (3), the human image and the depth image are one frame of video signals. In this step, the corresponding depth information is obtained via the infant image of the subject infant acquired by the image acquisition modules, and via the depth image of the subject infant acquired by the depth information acquisition modules. The depth information indicates the distances between each body part of the subject infant and the depth information acquisition modules, and is stored in a matrix. In the second embodiment of the present invention, the depth images are the main source of information, and others, such as the human images and the ultrasonic signals, are the secondary.

Figure 5:
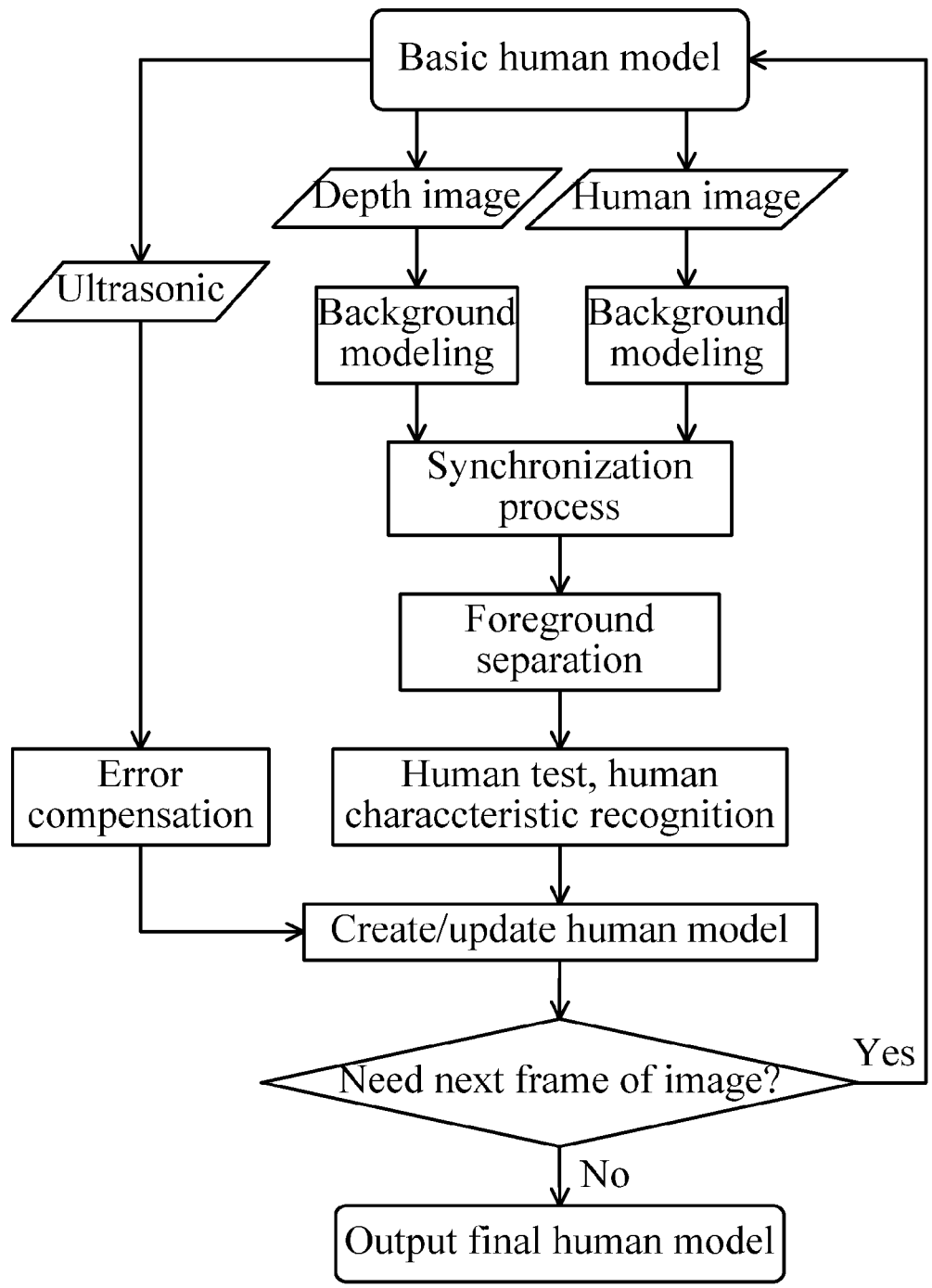
FIG. 5 is a schematic diagram of a e process of establishing an infant body model in a non-contact measuring method in pediatrics.

In Step (4), based on the data of the acquired image and the basic infant body model, the anthropometric characteristic points of the subject infant are calculated, and the infant body model is updated, thereby making the data of the acquired human image and the data of the acquired depth image adapted to each other. As shown in FIG. 5, the data acquisition and processing unit 1 in the non-contact measuring apparatus in pediatrics processes the human image and the depth image. The process of the processing comprises the following sub-steps: (41) A background modeling is executed via the depth image and the human image. For example, when Gaussian model is used for the background modeling, because in the measurement, the measurement background is relatively stable, but not constant, background modeling is required in the early data processing. (42) A synchronization process is executed to the human image and the depth image. The process comprises the matching process between the human image and the depth image. After the synchronization process, the human body in the human image and the human body in depth image are made in the same pose. (43) A foreground separation is executed based on the results of Step (41) and Step (42). By using the background obtained from Step (41), a foreground separation is executed to the data of the synchronized depth image and synchronized human image in Step (42), and the foreground prominence is obtained. Theoretically, the foreground prominence includes only the body of the subject infant. In the sub-step, the foreground can further be made more accurate and prominent by de-noising. (44) Torso detection is executed to the result obtained in Step (43) based on anthropometry, human anatomy knowledge, and information of size and aspect ratio. The torso is obtained from the foreground prominence, and the anthropometric characteristic points are calculated.

Between the foregoing Step (4) and Step (5), the following operations can be further performed. The hair thickness and cloth thickness of the infant are acquired. Based on the acquired hair thickness and cloth thickness, the infant body model is updated to compensate for errors caused by the hair and clothes. For instance, the position of the head vertex of the infant body model is corrected with the data of the hair thickness.

In Step (5), the completion of the updated infant body model is examined based on anthropometry. Furthermore, the stability of each anthropometric characteristic points is examined by using multi-frame human images and depth images based on video processing technology, which is specified as follows.

In human body measurements, the size and length of the body part of the subject between each joint are constant. In other words, there are certain invariances theoretically among anthropometric characteristic points. If the same subject was measured in a different frame (at different times), the invariances (indicators) calculated from the corresponding anthropometric characteristic points are close, the stability of the corresponding anthropometric characteristic points are determined to be good. If the invariances (indicators) calculated from the corresponding anthropometric characteristic points are largely different, the stability of the corresponding anthropometric characteristic points are determined to be poor. Completion of the human model can be examined with the stability of the anthropometric characteristic points. If all the anthropometric characteristic points are 100% stable, the corresponding human model is 100% complete. Completion herein can be a comprehensive consideration of stability of each anthropometric characteristic point.

In Step (6), the anthropometric data of the subject infant are calculated and obtained by using the anthropometric characteristic points to determine the positions of measurements in the human body, and combining the 3D surface models.

In addition, the non-contact measuring method provided by the present invention further comprises functions of self-learning and self-update. Specifically, Step (7) can be further included after Step (6). In Step 7, according to a result of the step (6), data in the infant body model database are updated by using an intermediate result and a final result of anthropometry.

The specific structure of the non-contact measuring apparatus in pediatrics is introduced above. In combination with the accompanying diagrams, the data processing process of the data acquisition and processing unit (1) in the non-contact measuring apparatus is described in detail as follows.

Figure 6:
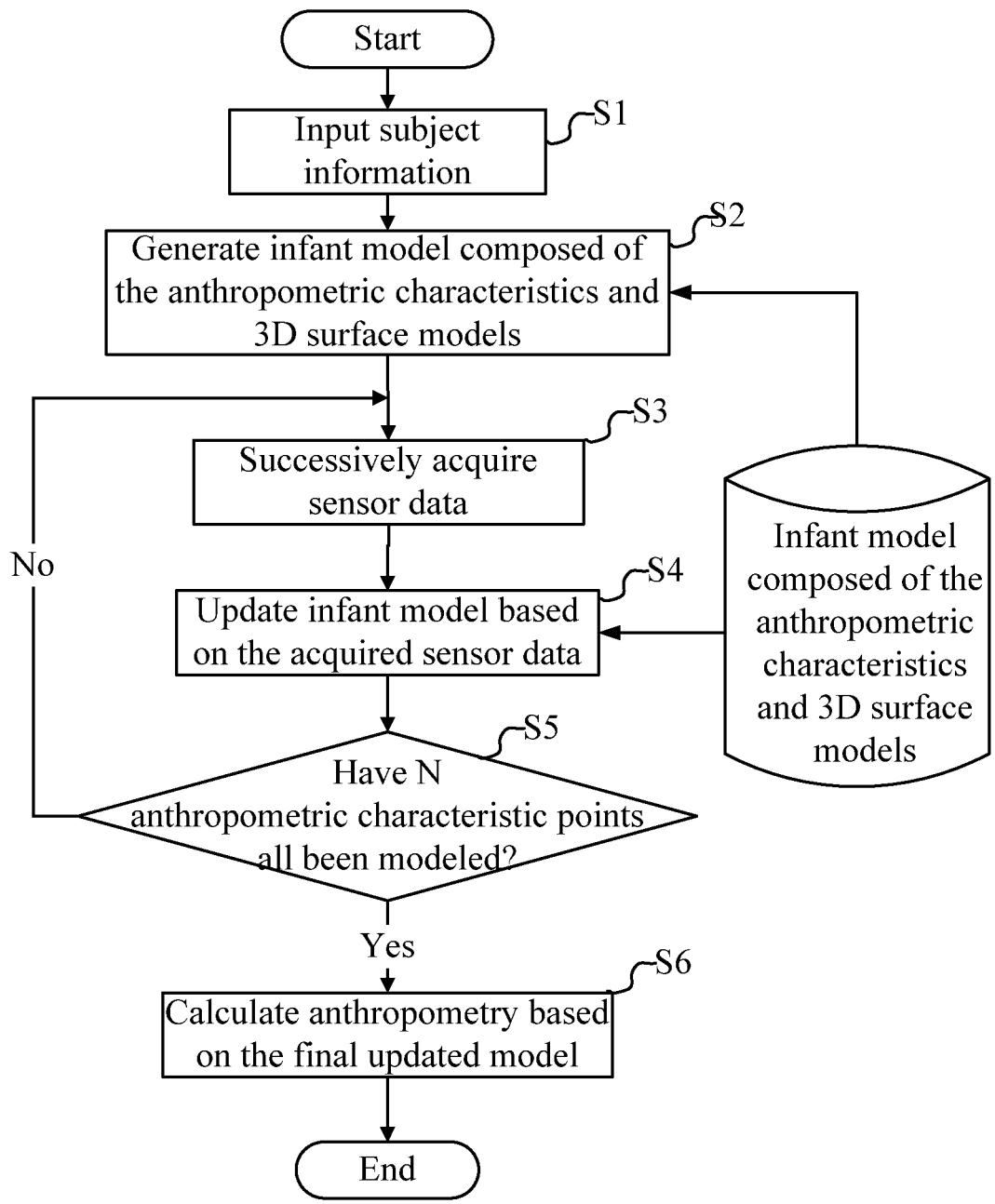
FIG. 6 is a data processing flow chart of a data acquisition and processing unit of a non-contact measuring apparatus in pediatrics in accordance with the present invention.

As shown in FIG. 6, Step S1: by hand or digital storage, the identity information of the subject infant is inputted to establish measurement files, such as names, dates of birth, age and other identity information. Subsequently, the process continues to Step S2.

Step S2: By the human images acquired by the image acquisition modules, and the 3D information acquired by the depth information modules, in combination with the built-in algorithm, the in initial infant body model is established. The infant body model is composed of the multiple anthropometric characteristic points and the 3D surface models. The infant body model is stored in the infant body model database. Then, the process continues to Step S3.

Step S3: The data are acquired through sensors. Then, the process proceeds to Step S4.

Step S4: Based on the data acquired by the sensors, the parameters of the infant body model are updated, and the updated infant body model is stored in the infant body model database. Then, the process proceeds to Step S5.

Step S5: Based on the infant body model stored in the database, whether the data of the certain number of anthropometric characteristic points are all used for modeling is determined If yes, the process continues to Step S6, and if not, the process returns to Step S3 for acquiring data through the sensors continuously.

Step S6: Based on the updated infant body model stored in the database, the calculation in anthropometry is executed, and the measurement results are obtained and outputted.

In Step S3 above, by acquiring the data through the image acquisition modules 3 and through the depth information collection modules 4, the image data and depth information are obtained. In Step S3, also, by acquiring the data through the ultrasonic sensors 2, the hair thickness and the cloth thickness are obtained, and the corrected infant body model is obtained through Step S4.

As shown in FIG. 3, in an embodiment of the non-contact measuring apparatus in pediatrics, the data output module is a monitor, on which the established infant body model is displayed, and a certain number of the anthropometric characteristic points are displayed synchronously. In Step S5, whether the modeling is complete or not is determined by examining whether the information of the positions of a certain number of the anthropometric characteristic points is all updated. In Step S6, after the modeling is complete, the infant body model in the monitor is measured and calculated anthropometrically based on the algorithm built in the data acquisition and processing unit, and then the data, such as height/length, head circumference and chest circumference, are obtained.

In summary, the non-contact measuring apparatus in pediatrics acquires the human images via the image acquisition modules, acquires the depth information via the depth information acquisition modules, establishes the infant body model via the data acquisition and processing unit, and finally obtains the anthropometric data based on the established infant body model. In the measuring process, the apparatus is not required to contact the infant's body or limbs, and there is no special requirement for the infant's pose, so that the measurement is easy to be performed. Moreover, by storing the infant body models and the measurement results, the anthropometric data on each stage of the infant can be combined together, and a curve of physical development of infants and young children can be drawn. In comparison with the local average growth curves, the development conditions of infants and young children can be followed, and pediatricians and parents can understand the development conditions of infants more easily and accurately.

The above describes the non-contact measuring method and apparatus in pediatrics provided by the present invention in detail. In terms of a person of ordinary skill in the art, any obvious changes made under the premise without departing from the true spirit of the invention will constitute an infringement of the patent right for invention, and will bear the corresponding legal responsibility.

What is claimed is:

1. A non-contact measuring method in pediatrics comprising steps of:
   (1) acquiring a human image of each body part of a subject infant using an image acquisition module and acquiring a depth image of the subject infant using a depth information acquisition module wherein the human image is a 2D color image containing the human body, the depth image is a grayscale image containing distance information between surface points in the view and the depth information acquisition module, and the human image and depth image are acquired without effective collaboration by the subject infant to follow instruction;
   (2) establishing an infant body model based on the acquired human image and depth image using 3D surface models and a data acquisition and processing unit when the data acquisition and processing unit analyzes the human image and the depth image, classifies each pixel in the depth image as a foreground pixel, which represents the subject infant, or a background pixel, obtains a size of the subject infant in term of the largest distance between two foreground pixels in the depth image, and adjusts the size of a basic infant body model corresponding to the size of the obtained subject infant wherein the infant body model is composed of multiple anthropometric characteristic points and 3D surface data, and a basic infant body model is an initial model prepared for further updating and is generated based on identity information and weight information of the subject infant;
   (3) acquiring data of a plurality of anthropometric characteristic points of the subject infant by the data acquisition and processing unit when the anthropometric characteristic point data are calculated using an algorithm program for anthropometry based on the acquired human image and depth image, and updating the infant body model based on the acquired anthropometric characteristic points when the data acquisition and processing unit adjusts the established infant body model using the acquired anthropometric characteristic point data for updating the body size, the head size and the ratios between the body parts of the established infant body model wherein the anthropometric characteristic point is a synonym for anthropometric landmark, defined for quantitative analysis on body size and the ratios between the body parts; and
   (4) obtaining an anthropometric measurement data of the subject infant from the updated infant body model when the data acquisition and processing unit uses the acquired anthropometric characteristic points to determine the measurement positions on the established infant body model and combines the 3D surface data of the established infant body model.

2. The non-contact measuring method in pediatrics as claimed in claim 1, wherein when the infant body model is being updated, hair thickness and cloth thickness are acquired and then the infant body model is updated based on the acquired hair thickness and the cloth thickness.

3. A non-contact measuring apparatus in pediatrics for performing the measuring method claimed in claim 1, the measuring apparatus comprising:
   a data acquisition and processing unit consisting of algorithm programs, for establishing and generating the basic infant body model, acquiring and calculating the anthropometric characteristic points; and for adjusting and updating the basic infant body model, examining the completeness of the infant body model, and obtaining the anthropometric data of the subject infant;
   one or more depth information acquisition modules coupled to the data acquisition and processing unit for acquiring the depth image of the subject infant;
   one or more image acquisition modules coupled to the data acquisition and processing unit; and
   a data output module bidirectionally coupled to the data acquisition and processing unit, for collecting identify information of the subject infant and displaying the measurement result to doctors or family members, or for printing the measurement results.

4. The non-contact measuring apparatus in pediatrics as claimed in claim 3, wherein the measuring apparatus further comprises one or more ultrasonic sensors for sensing a hair thickness and a cloth thickness and the ultrasonic sensors and the data acquisition and processing unit are bidirectionally coupled with each other.

5. The non-contact measuring apparatus in pediatrics as claimed in claim 3, wherein the measuring apparatus further comprises a bed for placing the subject infant, the depth acquisition module and the image acquisition module are respectively disposed above the top, head side and/or lateral side of the bed, ultrasonic sensors are respectively disposed at the end of the head side, on the lateral side or at the end of a foot side of the bed, a weighing sensor disposed under the bottom of the bed coupled with the data acquisition and processing unit.

6. A non-contact measuring method in pediatrics comprising steps of:
(1) inputting an identity information of a subject infant by a digital storage wherein the identity information comprises a name, gender, a date of birth and gestational age;
(2) generating a basic infant body model based on the identity information and a weight information of the subject infant using a data acquisition and processing unit, and an infant body model database, consisting of both genders, various races, various age ranges, and various gestational age ranges, when the data acquisition and processing unit analyzes a generic human body model set and the inputted identity information to select and generate the basic infant body model and the three-dimensional data, wherein the generic human body model is composed of multiple anthropometric characteristic points and 3D surface model;
(3) acquiring data of a human image of a subject infant using an image acquisition module and a depth image of the subject infant using a depth information acquisition module to measure distances between body parts of the subject infant wherein the human image is a single frame in a video and the depth image is a single frame in a depth video;
(4) calculating an anthropometric characteristic point of the subject infant using the data acquisition and processing based on the acquired data of human image and depth image and the basic infant body model or the updated infant body model, and updating the basic infant body model or the updated infant body model based on the calculated anthropometric characteristic point using the data acquisition and processing unit, when the infant body model is updated for a body size, a head size and ratios between body parts of the infant body model according to the anthropometric characteristic point calculated;
(5) examining whether the modelling of the infant body is complete using the data acquisition and processing unit to check stability of the updating process for the anthropometric characteristic points, when a quantity of adjustment, or a plurality of adjustments, on the infant body model is compared to the measurement stability requirement of the body size, the head size and the ratios, wherein the requirement is established based on clinic practices, returning to the step (3) to continuously acquire data of another frame of the depth image and another frame of the human image if the quantity of adjustment, or the adjustments, is greater than the measurement stability requirement and the updating process of infant body model is not stable and completed, and going to step (6) if the quantity of the adjustment, or the adjustments, is less than the measurement stability requirement and the updating process of infant body model is stable and complete; and
(6) obtaining an anthropometric measurement data of the subject infant from the updated infant body model when the data acquisition and processing unit uses the acquired anthropometric characteristic points to determine measurement positions on the infant body model established and combines 3D surface information of the infant body model.

7. The non-contact measuring method in pediatrics as claimed in claim 6, wherein:
when the infant body model is being updated, hair thickness and cloth thickness are acquired and then the infant body model is updated based on the acquired hair thickness and the cloth thickness.

8. The non-contact measuring method in pediatrics as claimed in claim 6, wherein the step (4) further comprising sub-steps of:
(41) executing a background modeling via the depth image and the human image;
(42) executing a synchronization process to the human image and the depth image;
(43) executing a foreground separation based on the step (41) and the step (42);
(44) executing torso detection to a result obtained in the step (43), calculating and determining each anthropometric characteristic points.

9. The non-contact measuring method in pediatrics as claimed in claim 6, wherein:
in the step (5), the stability of each anthropometric characteristic points is examined by using multi-frame human image and depth image based on video processing technology.

10. The non-contact measuring method in pediatrics as claimed in claim 6, wherein:
in the step (6), the anthropometric data of the subject infant are calculated and obtained by using the anthropometric characteristic point and the 3D surface model.

11. The non-contact measuring method in pediatrics as claimed in claim 6, wherein:
according to a result of the step (6), data in the infant body model database are updated by using an intermediate result and a final result of the anthropometry.

12. An non-contact measuring apparatus in pediatrics for performing the measuring method claimed in claim 6, the measuring apparatus comprising:
a data acquisition and processing unit, for generating a basic infant body model based on the identity information and a weight information of the subject infant, for calculating an anthropometric characteristic point of the subject infant based on the acquired data of the depth image and the human image and the basic infant body model, for updating the infant body model based on the calculated anthropometric characteristic point, for examining whether the infant body model is complete, and for obtaining an anthropometric data of the subject infant from the updated infant body model when the data acquisition and processing unit uses the anthropometric characteristic point to determine measurement positions in human body of the subject infant and combines the infant body model;
one or more depth information acquisition modules coupled to the data acquisition and processing unit for acquiring the depth image of the subject infant;
one or more image acquisition modules coupled to the data acquisition and processing unit, for acquiring the human image of the subject infant; and
a data output module bidirectionally coupled to the data acquisition and processing unit, for collecting identify information of the subject infant and displaying the measurement result to doctors or family members, or for printing the measurement results.

13. The non-contact measuring apparatus in pediatrics as claimed in claim 12, wherein the measuring apparatus further comprises one or more ultrasonic sensors for sensing a thickness of hair and a thickness of cloth, and the ultrasonic sensor and the data acquisition and processing unit are bidirectionally coupled with each other.

14. The non-contact measuring apparatus in pediatrics as claimed in claim 12, wherein the measuring apparatus further comprises a bed for placing the subject infant, the depth acquisition module and the image acquisition module are respectively disposed above the top, head side and/or lateral side of the bed, ultrasonic sensors are respectively disposed at the end of the head side, on the lateral side or at the end of a foot side of the bed, a weighing sensor disposed under the bottom of the bed coupled with the data acquisition and processing unit.

* * * * *